United States Patent [19]

Tanaka et al.

[11] Patent Number: 4,948,875

[45] Date of Patent: Aug. 14, 1990

[54] POLYPEPTIDE HAVING AN ANTI-TUMOR ACTIVITY AND A METHOD OF PREPARATION THEREOF

[75] Inventors: Shoji Tanaka; Masafumi Tsujimoto; Yayoi Wada; Nobuo Tsuruoka; Hiroshi Nakazato, all of Osaka, Japan

[73] Assignee: Suntory Limited, Osaka, Japan

[21] Appl. No.: 123,316

[22] Filed: Nov. 20, 1987

[30] Foreign Application Priority Data

Dec. 4, 1986 [JP] Japan .................................. 61-289514

[51] Int. Cl.[5] ............................................. C07K 13/00
[52] U.S. Cl. ..................................................... 530/350
[58] Field of Search ......................................... 530/350

[56] References Cited

U.S. PATENT DOCUMENTS 4,677,063  6/1987  Mark et al. ........................... 530/350

OTHER PUBLICATIONS

Pennica et al., *Nature*, vol. 312, pp. 724–729, (1984).
Beutler et al., *Nature*, vol. 316, pp. 552–554, (1985).
Beutler et al., *Nature*, vol. 320, pp. 584–588, (1986).
Old, *Science*, vol. 230, pp. 630–632, (1985).

*Primary Examiner*—Lester L. Lee
*Assistant Examiner*—Stephen B. Maebius
*Attorney, Agent, or Firm*—Cushman, Darby & Cushman

[57] ABSTRACT

Disclosed is a human TNF derivative with a reduced tendency to cause adverse side effects that is obtained by replacing the 31st and 32nd arginine residues from the N-terminal of the amino acid sequence of human TNF, which has a potential for causing serious adverse effects, with asparagine residue and threoine residue, respectively, as well as a method of preparing the same utilizing recombinant DNA technology.

1 Claim, 6 Drawing Sheets

Fig. 1

SEQUENCE OF NATURAL TYPE TNF

```
GTCAGATCATCTTCTCTCGAACCCCGAGTGACAAGCCTGTAGCCCATGTTGTAGCAAACCCT
 ValArgSerSerSerArgThrProSerAspLysProValAlaHisValValAlaAsnPro
+1                      10                          20
                                              CGCCGG
                                              ArgArg
CAAGCTGAGGGGCAGCTCCAGTGGCTGAACAACAACGGCCAATGCCCTCCTGGCCAATGGC
 GlnAlaGluGlyGlnLeuGlnTrpLeuAsnAsnThrAlaAsnAlaLeuLeuAlaAsnGly
                   30                          40
GTGGAGCTGAGAGATAACCAGCTGGTGGTGCCATCAGAGGGCCTGTACCTCATCTACTCC
 ValGluLeuArgAspAsnGlnLeuValValProSerGluGlyLeuTyrLeuIleTyrSer
                   50                          60
CAGGTCCTCTTCAAGGGCCAAGGCTGCCCCTCCACCCATGTGCTCCTCACCCACACCATC
 GlnValLeuPheLysGlyGlnGlyCysProSerThrHisValLeuLeuThrHisThrIle
                   70                          80
AGCCGCATCGCCGTCTCCTACCAGACCAAGGTCAACCTCCTCTCTGCCATCAAGAGCCCC
 SerArgIleAlaValSerTyrGlnThrLysValAsnLeuLeuSerAlaIleLysSerPro
                   90                         100
TGCCAGAGGGAGACCCCAGAGGGGCTGAGGCCAAGCCCTGGTATGAGCCCATCTATCTG
 CysGlnArgGluThrProGluGlyAlaGluAlaLysProTrpTyrGluProIleTyrLeu
                  110                         120
GGAGGGGTCTTCCAGTTGGAGAAGGGTGACCAGCCTGAGATCAATCGGCCCGAC
 GlyGlyValPheGlnLeuGluLysGlyAspArgLeuSerAlaGluIleAsnArgProAsp
                  130                         140
TATCTCGACTTTGCCGAGTCTGGGCAGGTCTACTTTGGGATCATTGCCCTG
 TyrLeuAspPheAlaGluSerGlyGlnValTyrPheGlyIleIleAlaLeu
                  150                    157
```

POLYPEPTIDE HAVING AN ANTI-TUMOR ACTIVITY AND A METHOD OF PREPARATION THEREOF

FIELD OF THE INVENTION

The present invention relates to a novel polypeptide having an anti-tumor activity wherein the polypeptide is prepared by modifying the structure of a known anti-tumor polypeptide that causes serious adverse side effects by utilizing recombinant DNA technology to reduce the incidence of adverse effects, and a method of preparation of this novel anti-tumor polypeptide utilizing recombinant DNA technology. More particularly, the present invention relates to a derivative of human tumor necrosing factor [hereinafter abbreviated as h-TNF (N1)], wherein the 31st and 32nd arginine residues from the N-terminal of the amino acid sequence of h-TNF (N1) are replaced with asparagine residue (Asn) and threonine residue (Thr), respectively, [this novel derivative will be abbreviated as TNF (Asn) hereinafter] and a method of preparation of TNF (Asn), wherein a gene coding for TNF (Asn) is linked with a vector expressed in *Escherichia coli*, and by culturing the prokaryotic cells transformed by the vector, the TNF (Asn) is obtained.

BACKGROUND OF THE INVENTION

Much has been expected from tumor necrosing factor (hereinafter abbreviated as TNF) since its discovery as an anti-tumor drug, because of its in vivo activity of causing hemorrhagic necrosis of various tumors without seriously affecting normal tissue cells, and also its in vitro activity of killing various tumor cells directly or inhibiting their growth. Pennica, et al. [Nature 312, 724–728 (1984)] isolated cDNA of human TNF, determined the amino acid sequence of human TNF, and reported its expression in *Escherichia coli* [hereinafter, the polypeptide having an amino acid sequence of human TNF found by Pennica, et al. is abbreviated as h-TNF (N1)]. It is well known that similar reports were subsequently made by other groups. Now that it is possible to obtain a highly purified TNF standard substance by DNA recombinant technology studies on the biological activities of TNF have been actively conducted. As a result, it has been revealed that TNF has, in addition to its known anti-tumor activity (tumoricidal activity and cytotoxic activity on hemangioendothelium), a wide variety of biological activities. Such biological activities include: (1) the activity of promoting growth of fibroblast cells; (2) the activation of leukocytes; (3) the activity of increasing the production of various cytokins (interleukin 1, interferon $\beta_2$, colony-stimulating factor); (4) the activity of increasing the production of prostaglandin $E_2$ and collagenase; (5) the activity of increasing the production of various membrane proteins; (6) the activity of increasing the absorption of bone and cartilage; and (7) differentiation-inducing activity.

As described above, it has been revealed that TNF possesses a wide variety of biological activities. Recently, Cerami, et al. pointed out an important factor in the clinical application of TNF as an anti-tumor agent. That is, Cerami, et al. found that, in the process of studying cachectin which is a causative agent of cachectic effects observed in serious or chronic infections or in cancer patients, TNF and cachectin are in fact identical substances [Beutler, et al., Nature, 316, 552–554 (1985)]. This fact implies that if TNF per se is applied clinically as an anti-tumor agent, a serious adverse effect (cachectic effect) will accompany it. At present, therefore, the development of TNF derivatives which have reduced cachectic effect is highly desirable.

BRIEF EXPLANATION OF THE DRAWINGS

FIG. 1 shows the amino acid sequence of TNF (Asn) and a nucleotide sequence of DNA coding for it.

FIG. 2 shows a method of preparation of M13mp19TNFRFDNA (RI/HindIII); FIG. 3 the same for M13mp19TNF (Asn) RF (RI/HindIII); and FIG. 4 the same for pIN5TNFST4 rop−(Asn) which expresses TNF (Asn).

DETAILED DESCRIPTION OF THE INVENTION

The present inventors prepared various derivatives of h-TNF (N1) by means of recombinant DNA technology and concentrated therein efforts on finding a TNF derivative in which anti-tumor activity is retained while the cachectic effect is reduced. As a result, the present inventors have found a novel TNF derivative which has a lower cachectic effect while retaining a similar level of anti-tumor activity in comparison with h-TNF (N1), and thus completed the invention. In other words, the present inventors have found that a TNF derivative [hereinafter abbreviated as TNF (Asn)], in which the 31st and 32nd arginine residues (Arg) from the N-terminal of the amino acid sequence of h-TNF (N1) are replaced with asparagine residue (Asn) and threonine residue (Thr), respectively, has remarkably lower lipoprotein lipase inhibiting activity, which is a measure of the cachectic activity of TNF, than that of h-TNF (N1), while a level of cytotoxic activity on hemangioendothelium, which is supposed to be strongly related to anti-tumor activity, which is similar to that of h-TNF (N1) is retained, and thus completed the invention.

In the following the present invention is illustrated further by examples and referential examples.

EXAMPLES

1. Preparation of a plasmid [pIN5TNFST4 rop− (Asn)] for production of TNF (Asn)

Figure 2:
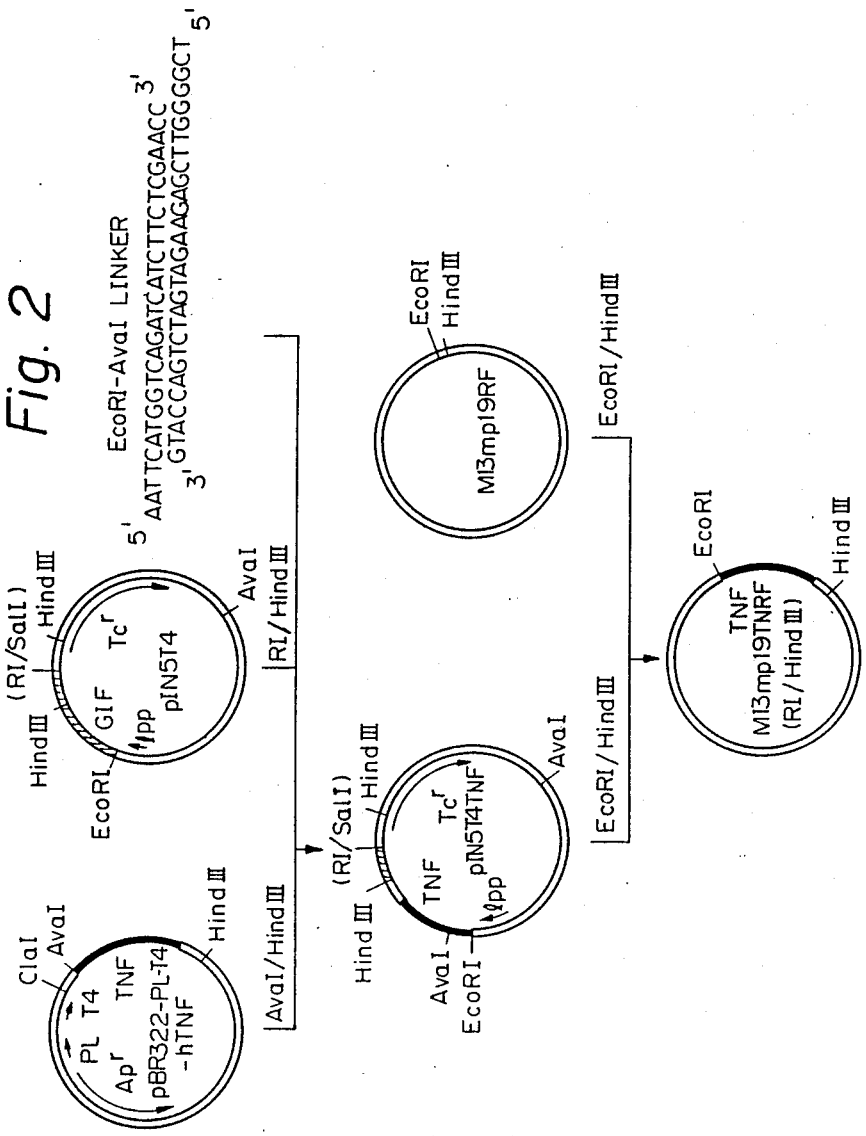
FIGS. 2–4 show the processes of various examples of plasmid preparation.

A plasmid for production of TNF (Asn) was prepared from the plasmid pBR322-PL-T4-hTNF expressing h-TNF (N1) (the *Escherichia coli* strain C600 in which said plasmid is introduced has been entrusted to The Culture Collection of Deutsch Sammlung von Mikroorganismen with the Accession No. DSM 3175) by the following method:

(A) Preparation of M13mp19TNFRF (RI/HindIII) (see FIG. 2)

3 μg of the plasmid pBR322-PL-T4-hTNF was digested completely with 10 Units (hereinafter abbreviated as U) of AvaI and 10 U of HindIII, and DNA fragments containing most of the TNF gene were isolated. On the other hand, 3 μg of the plasmid pIN5T4 (the method for preparation of this plasmid is disclosed in detail in European Patent Application, disclosed on 20 Mar., 1985, with Disclosure No. 0134673A1) was partially digested with 10 U of EcoRI and 10 U of HindIII and DNA fragments of 3.8 kb were isolated. DNA fragments obtained by these two processes and 1 μg of chemically synthesized DNA linker,

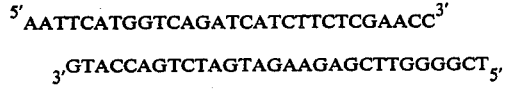

(Supplied from Applied Biosystem, 380A DNA synthesizer was used), which has ends cohesive to EcoRI and AvaI, respectively, were mixed and linked using 2 U of T4DNA ligase. Using the thus obtained reaction solution, the *Escherichia coli* strain W3110 was transformed and the desired plasmid pIN5T4TNF was obtained. Next, after complete digestion of 3 μg of the plasmid pIN5T4TNF using 10 U of EcoRI and 10 U of HindIII, DNA fragments containing TNF gene were isolated. On the other hand, 3 μg of M13mp19RF was digested completely using 10 U of EcoRI and 10 U of HindIII, and DNA fragments of 7.2 kb were isolated. DNA fragments obtained by these two processes were mixed and ligated using T4DNA ligase. and by transfecting the ligated product into the *Escherichia coli* strain JM103, the desired M13mp19TNFRF (RI/HindIII) was obtained.

Figure 3:
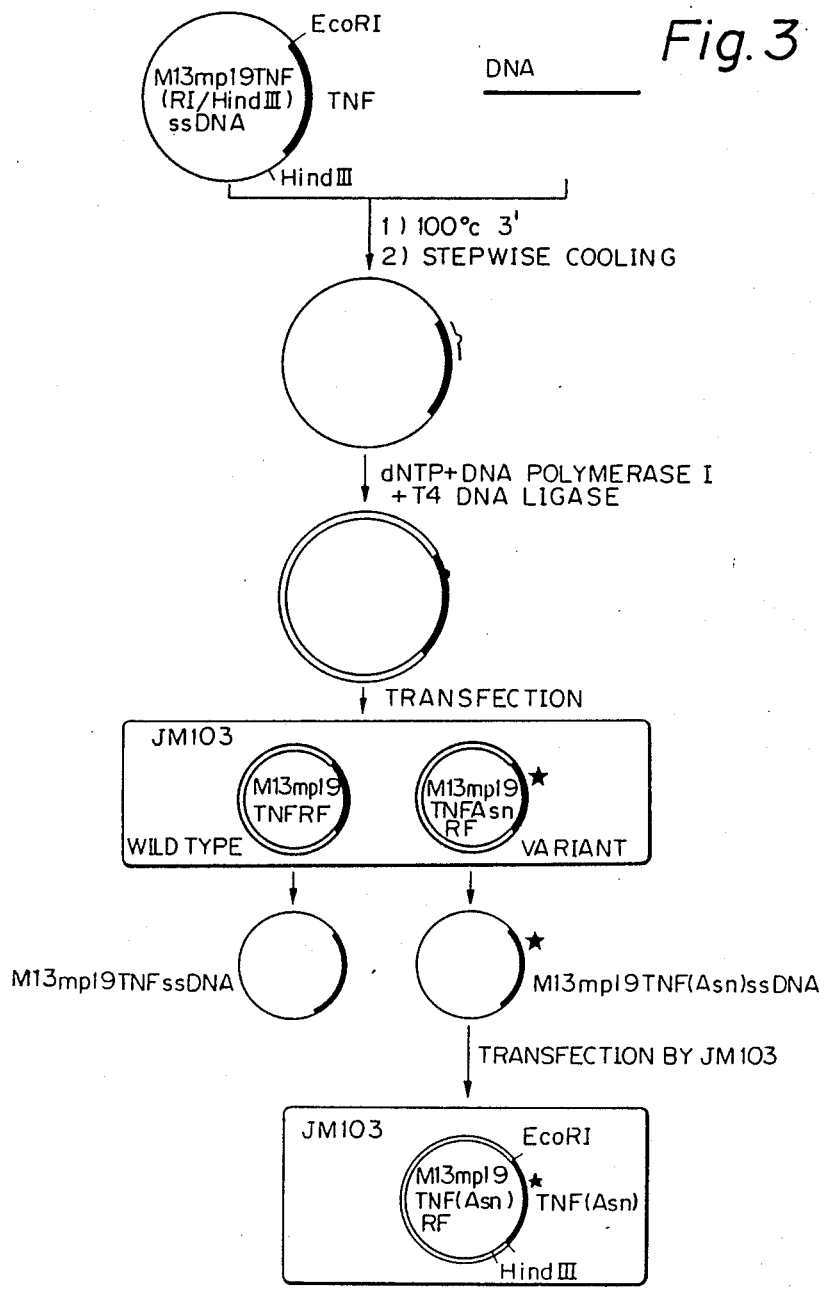

(B) Preparation of M13mp19TNF (Asn) RF (see FIG. 3)

One pmole of single stranded DNA of M13mp19TNFRF (RI/HindIII) and 10 pmole of chemically synthesized DNA (5'CTCCAGTGGCTGAACAACACGGCCAATGCCCTCC3') phosphorylated, were mixed and heated at 100° C. for 3 minutes, and then cooled down to room temperature over 2 hours for annealing. To this reaction solution, dNTP, DNA polymerase, ATP and T4DNA ligase were added and allowed to react, to make complete double-stranded cyclic DNA. The reaction solution thus obtained was used to transfect the DNA into the *Escherichia coli* strain JM103. Next, the desired clone was isolated and identified by plaque-hybridization according to the method of Benton, W. D. and Davis, R. W. [Science, 196, 180 (1977)]. Finally, DNA was isolated from the desired plaque and its nucleotide sequence was determined; thus M13mp19TNF (Asn) RF was obtained.

Figure 4:
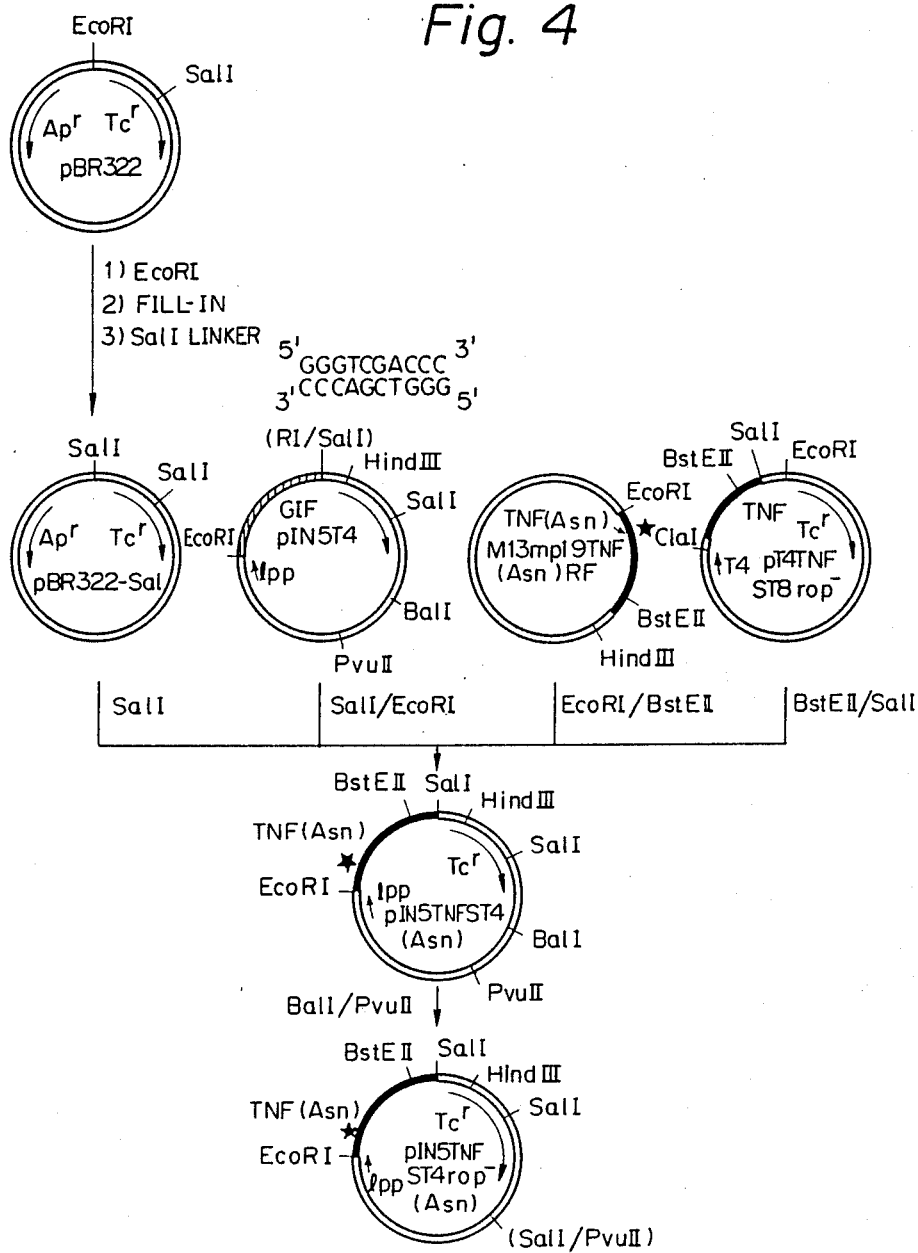

(C) Preparation of pIN5TNFST4 rop⁻ (Asn) (see FIG. 4)

In order to prepare the plasmid pIN5TNFST4 rop⁻ (Asn) expressing TNF (Asn), pIN5TNFST4 (Asn) plasmid was first prepared by combining the following four DNA fragments:

DNA fragment, 1: 3 μg of M13mp19TNF (Asn) RF was digested with 10 U of EcoRI and 10 U of BstEII and DNA fragments containing structural gene of TNF (Asn) of 400 bp long were isolated.

DNA fragment, 2: 5 μg of pT4TNFST8 rop⁻ (the method for preparation of this plasmid is disclosed in Japanese Patent Application No. 217740/1985) was digested completely using 10 U of BstEII and 10 U of SalI, and DNA fragments of 90 bp long were isolated.

DNA fragment, 3: 3 μg of pBR322 was cleaved with 5 U of EcoRI, and linear DNA fragments were collected. Using T4DNA polymerase and dNTP, the EcoRI-cohesive end of the DNA fragments was turned into a non-cohesive end and the DNA fragments were collected by ethanol precipitation. To this DNA, 1 μg of SalI linker

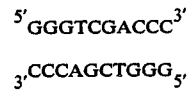

was added, and by using 1U of T4DNA ligase, the reaction gave pBR322-SalI plasmid. Next, 3 μg of pBR322-SalI was digested completely with 10 U of SalI, and DNA fragments of 650 bp long were isolated.

DNA fragment, 4: pIN5T4 (described above) was digested with 10 U of EcoRI and 10 U of SalI, and DNA fragments of 2.1 kbp long containing 1pp of promotor region were isolated. Four types of DNA fragments obtained above were linked together using T4DNA ligase, to give pIN5TNFST4 (Asn).

Next, a plasmid expressing TNF (Asn) very effectively, pIN5TNFST4 rop⁻ (Asn), in which the rop (repressor of primer) region, deriving from pBR322 and controlling replication of pIN5TNFST4 (Asn) plasmid, was removed so that the number of plasmid copies could be increased, was prepared in the following way: 3 μg of pIN5TNFST4 (Asn) was cleaved with 10 U of BalI and 10 U of PvuII, and DNA fragments of 3.2 kbp long were isolated. After that, they were allowed to be cyclized. Using this reaction solution, the *Escherichia coli* strain W3110 was transformed, and DNAs were isolated from the clone which showed tetracycline resistance. Using a routine method, this DNA was analysed and the desired plasmid, in which BalI-PvuII DNA fragment of 600 bp long was removed from pIN5TNFST4 (Asn), pIN5TNFST4 rop⁻ (Asn) was obtained.

2. Preparation of recombinant *Escherichia coli* strain W3110/pIN5TNFST4 rop⁻ (Asn), expressing TNF (Asn)

The desired recombinant *Escherichia coli* strain W3110/pIN5TNFST4 rop⁻ (Asn), expressing TNF (Asn), was obtained by collecting tetracycline resistant clone after transforming the *Escherichia coli* strain W3110 by introduction of said pIN5TNFST4 rop⁻ (Asn) plasmid.

The transformed *Escherichia coli* strain was named SBM287, and was deposited under the Budapest Treaty at the Fermentation Research Institute (one of the International Depositary Authorities) with Accession No. FERM BP-1544.

3. Purification of TNF (Asn)

TNF (Asn) producing recombinant *Escherichia coli* [W3110/pIN5TNFST4 rop⁻ (Asn)] was cultured in 800 ml of GC culture medium (2% glycerine, 3% casamino acid, 0.5% sodium dihydric phosphage, 0.2% yeast extract, 0.15M sodium hydroxide, 0.1% MgSO₄.7-H₂O, pH 6.5) in the presence of tetracycline (10 μg/ml) at 37° C. for 17 hours. Next, bacterial cells were collected by centrifugation and suspended in 10 mM Tris-HCl buffer solution (pH 8.0). After that, the cells were disrupted with a French press under cooling, and the suspension was centrifuged at 8000 rpm for 20 minutes, 150 ml of supernatant being obtained. Using this crude extract solution, TNF (Asn) was purified in the following way: First, said crude extract solution was passed through DEAE Sephallose FF (Pharmacia, φ 2.5×8 cm), a support for anion exchange chromatography equilibrated with 20 mM Tris-HCl buffer solution (pH 7.4), and after washing well with the same buffer solution, a solution containing a linear gradient of sodium chloride concentration from 0M to 0.5M was passed, and fractions eluted at around 0.15M were collected; thus, the desired fractions containing TNF (Asn) were obtained. Next, ammonium sulfate was added to these fractions to give a solution 30% saturated with ammonium sulfate, and the solution was passed through Phenylsephallose 4B (Pharmacia, φ1.0×15 cm), a hydrophobic support for chromatography, equilibrated well with 20 mM Tris-HCl buffer solution (pH 7.4) containing 30%-saturated ammonium sulfate. After washing well with the same buffer solution, a solution containing a linear gradient of ammonium sulfate concentration (from 30% saturation to 0%) and ethylene glyool (from 0% to 50%) and the desired substance was eluted around 20%-saturated ammonium sulfate solution. After the obtained fractions were dialyzed well with 20 mM Tris-HCl buffer solution (pH 7.4), they were passed through S Sephallose FF (Pharmacia, φ1.0×15 cm), a support for cation exchange chromatography was equilibrated with the same solution, and after being washed well with the same solution, a solution containing a linear gradient of sodium chloride concentration from 0M to 0.5M was allowed to pass to have the desired substance [TNF (Asn)]eluted around 0.2M sodium chloride. The TNF (Asn) standard substance obtained in this way shows a single band on SDS-PAGE, and the results of amino acid analysis were satisfactorily consistent with the theoretical values.

4. Biological activity of TNF (Asn)

The biological characteristics (lipoprotein lipase inhibiting activity and cytotoxic activity on hemangioendothelium) of TNF (Asn) obtained in Example 3 were compared with those of h-TNF (N1) as in the following: [h-TNF (N1) used here is TNF obtained from the transformed *Escherichia coli* strain W3110/pT4TNFST8 rop⁻ disclosed in Japanese Patent Application No. 295140/1985, by a method similar to the one described in Example 3].

(A) Lipoprotein lipase inhibiting activity

Lipoprotein lipase inhibiting activity which is an in vitro measure of cachectin effect was determined by the method described by Kawakami, et al. (Kawakami, et al., Proc. Nat. Acad. Sci. U.S.A., 79, 912–916, 1982).

Figure 5:
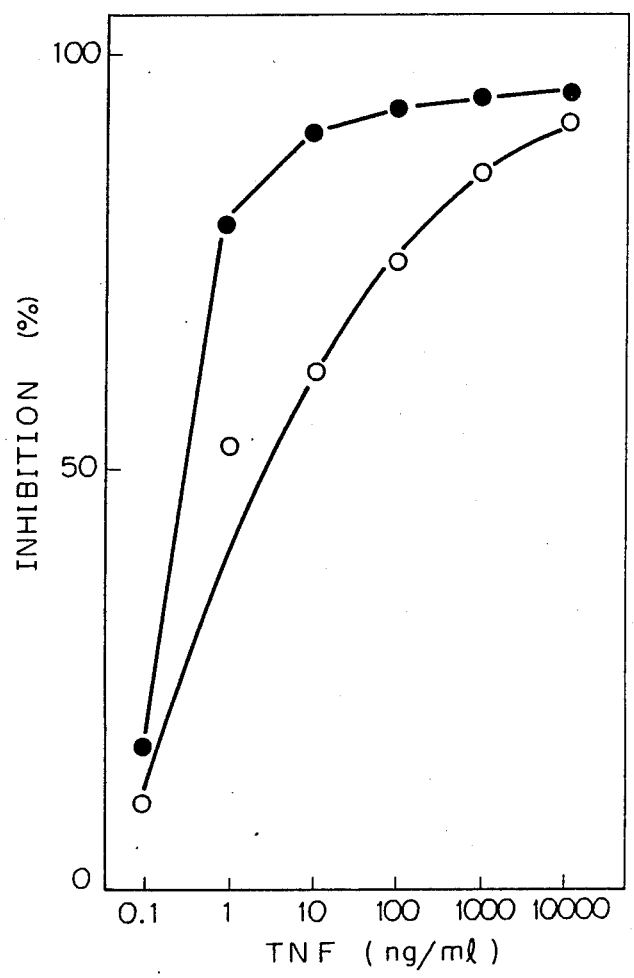
FIG. 5 shows the lipoprotein lipase activity of h-TNF (N1) (●) and TNF (Asn) (○).

In other words, 3T3-L1 lipocyte precursor cells were cultured in a modified Dalbecco's Eagle (DME) medium containing 10% fetal bovine serum (FBS) until the cells were in a confluent state. The cells were cultured for another two days, and then further cultured in the DME medium containing 10% FBS, 10 μg/ml of bovine insulin, 0.5 mM of methylisobuthylxanthine and 1.0 μM of dexamethasone for 48 hours. After that, the cells were cultured in DME medium containing 50 ng/ml of bovine insulin for 4 days. After these cells were cultured in DME medium containing 10% FBS for 20 hours in the presence of h-TNF (N1) or TNF (Asn), the culture solution was discarded and 10 U/ml of heparin-containing DME medium was added. The cells were then cultured for 1 hour. In this way, lipoprotein lipase bound to the membrane was released in the culture supernatant. To 75 μl of this supernatant, 25 μl of 200 mM Tris-HCl buffer solution (pH 8.1) containing 22.6 mM of tritium-labelled triolein, 2.5 mg/ml of lecithin, 40 mg/ml of bovine serum albumine, 33% (v/v) of rat normal serum and 33% (v/v) of glycerol was added and the mixture was allowed to react at 37° C. for 30 minutes. The amount of fatty acid released was then determined. The results showed that, as shown in FIG. 5, TNF (Asn) has a clearly lower lipoprotein lipase inhibiting activity than that of h-TNF (N1). [When comparison is made with the $IC_{75}$, the lipoprotein lipase inhibiting activity of TNF (Asn) is not more than 1/100 of the same of h-TNF (N1).] "IC" is an abbreviation of Inhibition Concentration, and $IC_{75}$ denotes the concentration at which 75% of the growth is inhibited.

(B) Cytotoxic activity on hemangioendothelium

The cytotoxic activity on hemangioendothelium was determined by the activity of inhibiting the growth of bovine hemangioendothelial cells [prepared by the method of Sato, et al., Journal of National Cancer Institute (JNCI), 76, 1113–1121 (1986)].

Figure 6:
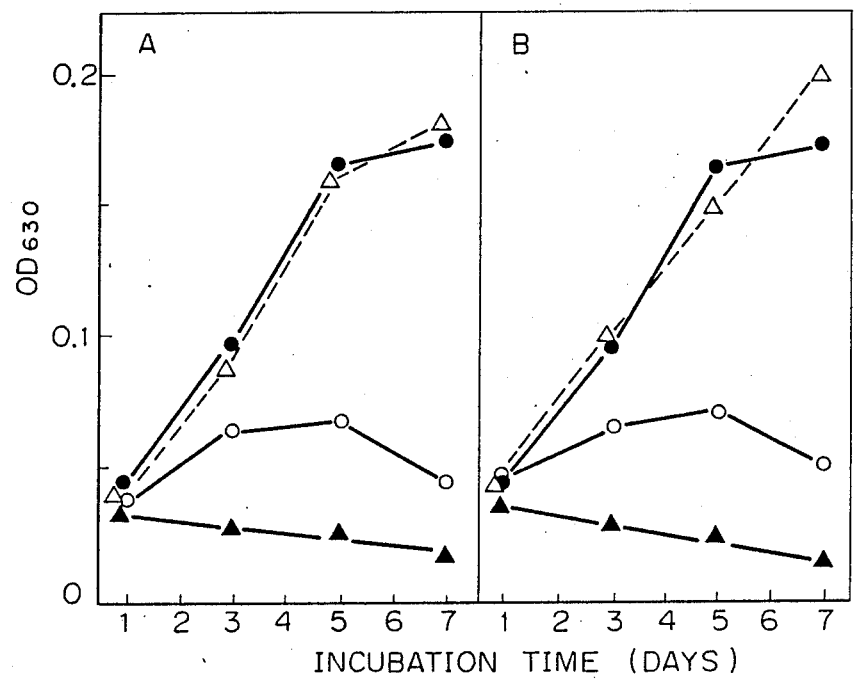
FIG. 6 shows the growth-inhibiting activity of h-TNF (N1) (A) and TNF (Asn) (B) on hemangioendothelial cells. In the figure, ● shows the growth pattern of hemangioendothelial cells in the absence of said TNF, ○ and ▲ show the same in the presence of 1 ng/ml and 10 ng/ml of said TNF, respectively, and Δ shows the same in the presence of 5 μg/ml of monoclonal antibody (neutralizing antibody) against h-TNF (N1).

Specifically, these endothelial cells were placed in a 96-well microplate so that each well contained 8,000 cells, and cultured in Eagle MEM medium containing 10% fetal bovine serum in the presence of h-TNF (N1) and TNF (Asn). Next, each cell was fixed in 10% formaline for 15 minutes, and dyed with 0.05% naphthol blue black for 30 minutes. After washing the plate well with water and drying it, the dye was extracted with 50 mM of sodium hydroxide, and absorbance at 630 nm was determined. The results showed that, as shown in FIG. 6, the cytotoxicity of TNF (Asn) on hemangioendothelium is equivalent to that of h-TNF (N1).

The results of studies on biological activities showed that the polypeptide of the present invention, TNF (Asn), is a TNF derivative very useful as a drug, which has a potent anti-tumor activity without being accompanying by any serious adverse effects (cachectic effects).

What is claimed is:

1. A novel polypeptide having the following amino acid sequence:

X—ValArgSerSerSerArgThrProSerAspLysProValAlaHisVal
                                                10

ValAlaAsnProGlnAlaGluGlyGlnLeuGlnTrpLeuAsn<u>AsnThr</u>Ala
       20                                              30

AsnAlaLeuLeuAlaAsnGlyValGluLeuArgAspAsnGlnLeuValVal
                   40                                  50

ProSerGluGlyLeuTyrLeuIleTyrSerGlnValLeuPheLysGlyGln
                              60

GlyCysProSerThrHisValLeuLeuThrHisThrIleSerArgIleAlaVal
       70                                       80

SerTyrGlnThrLysValAsnLeuLeuSerAlaIleLysSerProCysGlnArg
            90                              100

GluThrProGluGlyAlaGluAlaLysProTrpTyrGluProIleTyrLeu
                  110                              120

GlyGlyValPheGlnLeuGluLysGlyAspArgLeuSerAlaGluIleAsn
                         130

ArgProAspTyrLeuAspPheAlaGluSerGlyGlnValTyrPheGlyIle
       140                                 150

IleAlaLeu—OH wherein X denotes a hydrogen atom or a methionine residue.

* * * * *